(12) United States Patent
Kusukawa (10) Patent No.: US 7,836,889 B2
(45) Date of Patent: Nov. 23, 2010

(54) AIRWAY ESTABLISHMENT APPARATUS AND STEPLESS CONTROLLER TO BE USED THEREIN

(75) Inventor: Jingo Kusukawa, Kurume (JP)

(73) Assignee: Kurume University, Fukuoka (JP)

( * ) Notice: Subject to any disclaimer, the term of this patent is extended or adjusted under 35 U.S.C. 154(b) by 453 days.

(21) Appl. No.: 11/793,766

(22) PCT Filed: Dec. 27, 2005

(86) PCT No.: PCT/JP2005/023903

§ 371 (c)(1),
(2), (4) Date: Oct. 10, 2007

(87) PCT Pub. No.: WO2006/070805

PCT Pub. Date: Jul. 6, 2006

(65) Prior Publication Data

US 2008/0105268 A1    May 8, 2008

(30) Foreign Application Priority Data

Dec. 28, 2004    (JP) ............................. 2004-380947

(51) Int. Cl.
*A61F 5/56* (2006.01)
*A61C 5/14* (2006.01)
*A61C 3/00* (2006.01)

(52) U.S. Cl. ............................. 128/848; 128/859; 433/6

(58) Field of Classification Search .................. 128/848, 128/859–862; 433/3, 6, 7, 140; 602/902
See application file for complete search history.

(56) References Cited

U.S. PATENT DOCUMENTS

| 5,983,892 | A | 11/1999 | Thornton |
| 6,055,986 | A | 5/2000 | Meade |
| 7,448,388 | B2 * | 11/2008 | Halstrom .................... 128/861 |
| 2001/0047805 | A1 | 12/2001 | Scarberry et al. |
| 2005/0175954 | A1 * | 8/2005 | Zacher ......................... 433/5 |

FOREIGN PATENT DOCUMENTS

| GB | 2 389 796 | 12/2003 |
| JP | 07-241341 | 9/1995 |

* cited by examiner

*Primary Examiner*—Patricia M Bianco
*Assistant Examiner*—Ophelia Hawthorne
(74) *Attorney, Agent, or Firm*—Wenderoth, Lind & Ponack, L.L.P.

(57) ABSTRACT

Provided is an airway maintenance apparatus that draws the lower jaw forward to forcibly maintain an airway during sleep, designed to allow quick and easy setting of a drawing extent for the lower-jaw side attachment suitable for each patient. The airway maintenance apparatus contains an upper-jaw side attachment 1 to be attached to the upper jaw side in the oral cavity, and a lower-jaw side attachment 2 provided separately from the upper-jaw side attachment 1, and to be attached to the lower jaw side in the oral cavity, the lower-jaw side attachment 2 being connected to the upper-jaw side attachment 1 via a stepless adjusting device 3 capable of moving the lower-jaw side attachment 2 in a stepless manner in the direction of drawing the lower jaw forward relative to the upper-jaw side attachment 1.

4 Claims, 5 Drawing Sheets

000# AIRWAY ESTABLISHMENT APPARATUS AND STEPLESS CONTROLLER TO BE USED THEREIN

TECHNICAL FIELD

The present invention relates to an apparatus for forcibly maintaining airway by drawing the lower jaw forward during sleep, and a stepless adjusting device to be used therein. More specifically, the present invention relates to an airway maintenance apparatus designed to allow quick and easy setting of a drawing extent for the lower-jaw side attachment suitable for each patient, and a stepless adjusting device to be used therein.

BACKGROUND ART

Sleep apnea syndrome (SAS) is a disease characterized by multiple episodes of cessation of respiration (apnea) during sleep, resulting from partial or complete obstruction of the airway by the root of the tongue and/or the soft palate falling down therein. As a result, sleep is disturbed and daytime sleepiness occurs; in recent years, a large number of accidents attributable to this disease, including driving a car asleep, have been reported.

Traditionally, a measure against sleep apnea syndrome has been taken, in which the lower jaw is slightly drawn (pulled) forward from the normal occlusal position to forcibly maintain an airway, so as to prevent apnea during sleep. The lower jaw is usually drawn forward using a dedicated airway maintenance apparatus (hereinafter sometimes referred to as "mouthpiece") set in the oral cavity.

As such a mouthpiece, for example, one disclosed in patent document 1 is known. This mouthpiece comprises an upper-jaw side attachment to be attached to the upper jaw side (referred to as "upper mold" in patent document 1) and a lower-jaw side attachment to be attached to the lower jaw side (referred to as "lower mold" in patent document 1), and has a structure in which the lower-jaw side attachment is fixed in a unified way to the upper-jaw attachment with a shift toward the front face side from the normal occlusal position.

In addition, for example, one disclosed in non-patent document 1 is also known. This mouthpiece comprises an upper-jaw side attachment and a lower-jaw side attachment in a separable way, and has a structure in which the attachment position of the lower-jaw side attachment to the upper-jaw side attachment can be adjusted stepwise.

An airway is maintained by drawing the lower jaw forward using the mouthpiece disclosed in patent document 1 or non-patent document 1.

Patent document 1: Japanese Patent Unexamined Publication No. HEI-7-241341

Non-patent document 1: Catalogue of Panasonic Dental Co., Ltd., "Anti-snoring Mouthpiece Thrasnore™" Internet <URL: http://panasonic.co.jp/healthcare/dental/products/pdf/therasnore.pdf>

DISCLOSURE OF THE INVENTION

Problems to be Solved by the Invention

However, the above-described conventional mouthpieces pose the problems described below.

The drawing extent for the lower jaw for maintaining an airway differs among individual patients, and cannot be standardized by, for example, determining the number of millimeters by which the lower jaw is drawn forward to maintain a desired airway. Therefore, the position for attaching the lower-jaw side attachment to maintain a desired airway is determined by changing the drawing extent relative to the upper-jaw side attachment little by little to find the appropriate position for each patient.

Hence, in the case of the mouthpiece disclosed in patent document 1, fixation and attachment/detachment of the upper-jaw side attachment and the lower-jaw side attachment must be repeated frequently until the appropriate position for attaching the lower-jaw side attachment relative to the upper-jaw side attachment, and, in addition, because the appropriateness of the position for attaching the lower-jaw side attachment cannot be confirmed unless the patient actually falls asleep and experiences apnea, the patient unavoidably frequently falls asleep and awakes. Hence, the mouthpiece disclosed in patent document 1 requires much labor and time for preparation and imposes a major burden on the patient.

Since the mouthpiece disclosed in non-patent document 1 is configured to allow the separation of the upper-jaw side attachment and the lower-jaw side attachment, and to allow stepwise adjustment of the position for attaching the lower-jaw side attachment, at first glance it seems that the position for attaching the lower-jaw side attachment can be easily found. However, the appropriate drawing extent for the lower jaw for maintaining a desired airway differs among different patients as described above, and is not applicable to some patients at all.

In the case of this mouthpiece as well, the patient must be awaken up at the time of adjusting the position of the lower-jaw side attachment; therefore, a major burden is imposed on the patient as with the above-described mouthpiece.

It is an object of the present invention to provide an airway maintenance apparatus designed to allow the quick and easy setting of a drawing extent for the lower-jaw side attachment suitable for each patient, and a stepless adjusting device to be used therein.

It is another object of the present invention to provide an airway maintenance apparatus designed to allow the drawing extent for the lower-jaw side attachment to be adjusted in a stepless manner, so as to accommodate many patients, and a stepless adjusting device to be used therein.

It is still another object of the present invention to provide an airway maintenance apparatus designed to allow the drawing extent for the lower-jaw side attachment to be adjusted without taking out the apparatus from the oral cavity, and without waking up the patient, and a stepless adjusting device to be used therein.

It is still yet another object of the present invention to provide an airway maintenance apparatus designed to allow obtainment of a desired airway with a small drawing extent, and a stepless adjusting device to be used therein.

It is a further object of the present invention to provide an airway maintenance apparatus capable of preventing dryness in the oral cavity during use and entry of foreign matter in the oral cavity during use, and a stepless adjusting device to be used therein.

Means of Solving the Problems

To accomplish the above-described objects, the present invention involves the means described below.

Provided in a first mode of embodiment of the present invention is an airway maintenance apparatus for drawing the lower jaw forward to forcibly maintain an airway, comprising an upper-jaw side attachment to be attached to the upper jaw side in the oral cavity, and a lower-jaw side attachment to be attached to the lower jaw side in the oral cavity, provided separately from the upper-jaw side attachment, the lower-jaw side attachment being connected to the upper-jaw side attachment via a stepless adjusting device capable of moving in a stepless manner in the direction of drawing the lower jaw forward relative to the upper-jaw side attachment.

Provided in a second mode of embodiment of the present invention is the airway maintenance apparatus according to the first invention, wherein the lower-jaw side attachment is configured to allow the lower jaw to be drawn forward while the upper-jaw side attachment and the lower-jaw side attachment are attached.

Provided in a third mode of embodiment of the present invention is the airway maintenance apparatus according to the first or second invention, wherein the lower-jaw side attachment is connected to allow the lower jaw to be drawn obliquely upwardly.

Provided in a fourth mode of embodiment of the present invention is the airway maintenance apparatus according to the first, second or third invention, provided with a blocker that blocks or substantially blocks the gap between the upper-jaw side attachment and the lower-jaw side attachment formed at the time they are attached.

Provided in a fifth mode of embodiment of the present invention is the airway maintenance apparatus according to the first, second, third or fourth invention, wherein the stepless adjusting device comprises a bolt member provided with a turn operation portion at one end of the screw portion thereof, a bolt member retainer mounted on one attachment, and formed to allow the penetration of the screw portion of the bolt member to penetrate, and not to allow the penetration of the turn operation portion, a nut member mounted on the other attachment, in which the screw portion of the bolt member penetrated by the bolt member retainer can be screwed, the bolt member is formed not to allow the axial movement thereof relative to the bolt member retainer, and the lower-jaw side attachment can be moved forward and backward relative to the upper-jaw side attachment by turning the bolt member in a state screwed in the nut member.

Provided in a sixth mode of embodiment of the present invention is the airway maintenance apparatus according to the first, second, third, or fourth invention, wherein the stepless adjusting device comprises a bolt member provided with a turn operation portion at one end of the screw portion thereof, a bolt member retainer mounted on the upper-jaw side attachment in a vertically rotatable manner, and formed to allow the penetration of the screw portion of the bolt member, and not to allow the penetration of the turn operation portion, a nut member mounted on the lower-jaw side attachment, in which the screw portion of the bolt member penetrated by the bolt member retainer can be screwed, and a fixing means for fixing the bolt member retainer to the upper-jaw side attachment at a specified angle, wherein the bolt member is formed not to allow the axial movement thereof relative to the bolt member retainer, and the lower-jaw side attachment can be moved forward and backward relative to the upper-jaw side attachment by turning the bolt member in a state screwed in the nut member.

Provided in a seventh mode of embodiment of the present invention is a stepless adjusting device to be used as mounted on the airway maintenance apparatus according to the first, second, third, fourth, fifth or sixth invention, wherein the lower-jaw side attachment can be moved in a stepless manner in the direction of drawing the lower jaw forward relative to the upper-jaw side attachment.

Provided in an eighth mode of embodiment of the present invention is a stepless adjusting device to be used as mounted on the airway maintenance apparatus according to the first, second, third, fourth, fifth or sixth invention, comprising a bolt member provided with a turn operation portion at one end of the screw portion thereof, a bolt member retainer that can be mounted on one attachment, and formed to allow the penetration of the screw portion of the bolt member, and not to allow the penetration of the turn operation portion, and a nut member that can be amounted on the other attachment, in which the screw portion of the bolt member penetrated by the bolt member retainer can be screwed, wherein the bolt member is formed not to allow the axial movement thereof relative to the bolt member retainer, and the lower-jaw side attachment can be moved forward and backward relative to the upper-jaw side attachment by turning the bolt member in a state screwed in the nut member.

Provided in a ninth mode of embodiment of the present invention is a stepless adjusting device to be used as mounted on the airway maintenance apparatus according to the first, second, third, fourth, fifth or sixth invention, comprising a bolt member provided with a turn operation portion at one end of the screw portion thereof, a bolt member retainer mounted on the upper-jaw side attachment in a vertically rotatable way, and formed to allow the penetration of the screw portion of the bolt member, and not to allow the penetration of the turn operation portion, a nut member mounted on the lower-jaw side attachment, in which the screw portion of the bolt member penetrated by the bolt member retainer can be screwed, and a fixing means for fixing the bolt member retainer to the upper-jaw side attachment at a specified angle, wherein the bolt member is formed not to allow the axial movement thereof relative to the bolt member retainer, and the lower-jaw side attachment can be moved forward and backward relative to the upper-jaw side attachment by turning the bolt member in a state screwed in the nut member.

According to the present invention, the lower jaw can be drawn forward to forcibly maintain an airway during sleep, so as to, for example, prevent sleep apnea syndrome and snoring.

(Effect)

The present invention comprises an upper-jaw side attachment and a lower-jaw side attachment connected via a stepless adjusting device, and is used with the upper-jaw side attachment attached to the upper jaw side in the oral cavity, and the lower-jaw side attachment attached to the lower jaw side. By operating the stepless adjusting device, the lower-jaw side attachment and the lower jaw wearing the same can be drawn forward in a stepless manner relative to the upper-jaw side attachment.

In a configuration wherein the lower-jaw side attachment can be drawn forward while wearing the upper-jaw side attachment and the lower-jaw side attachment, the lower jaw can be drawn forward while wearing the lower attachment.

In a configuration wherein the lower-jaw side attachment is connected to the upper-jaw side attachment to allow the lower jaw to be drawn obliquely upwardly, an airway can be maintained by drawing the lower jaw obliquely upwardly.

In a configuration wherein a blocker is provided, the gap between the upper-jaw side attachment and the lower-jaw side attachment can be blocked by the blocker.

In a configuration wherein the stepless adjusting device comprises a bolt member, a bolt member retainer, and a nut member, the lower-jaw side attachment and the upper-jaw side attachment are connected by screwing the screw portion of the bolt member in the nut member through the bolt member retainer. Then, by turning the bolt member in a state screwed in the nut member, the lower-jaw side attachment can be moved forward and backward relative to the upper-jaw side attachment.

In a configuration wherein the stepless adjusting device comprises a bolt member, a bolt member retainer, and a nut member, the bolt member retainer being amounted on the upper-jaw side attachment to allow the vertical rotation thereof and fixation at a specified angle, the direction of moving forward and backward of the lower-jaw side attachment can be changed by fixing the bolt member retainer at the specified angle.

Effects of the Invention

The present invention is configured as described above, and has the effects described below.

(a) According to the present invention, because the lower-jaw side attachment and the lower jaw wearing the same can be drawn forward in a stepless manner relative to the upper-jaw side attachment by operating the stepless adjusting device, a drawing extent for the lower-jaw side attachment suitable for each patient can be quickly and easily set. Additionally, since the drawing extent for the lower-jaw side attachment can be adjusted in a stepless manner, the drawing extent relative to the upper-jaw side attachment can be easily changed little by little, so as to accommodate many patients.

(b) In the configuration wherein the lower-jaw side attachment can be drawn forward while wearing the upper-jaw side attachment and the lower-jaw side attachment, the drawing extent for the lower-jaw side attachment can be adjusted without taking out the apparatus from the oral cavity, and without waking the patient in sleep.

(c) In the configuration wherein the lower-jaw side attachment is connected to the upper-jaw side attachment to allow the lower jaw to be drawn obliquely upwardly, the burden on the patient can be lessened since a wide airway for the drawing extent can be maintained by drawing the lower jaw obliquely upwardly.

(d) In the configuration wherein a blocker is provided, the gap between the upper-jaw side attachment and the lower-jaw side attachment can be blocked by the blocker to prevent dryness in the oral cavity during use, and to prevent entry of foreign matter in the oral cavity during use.

(e) In the configuration wherein the stepless adjusting device comprises a bolt member, a bolt member retainer, and a nut member, the bolt member retainer being mounted on the upper-jaw side attachment to allow the vertical rotation thereof, and fixation at a specified angle, the direction of moving forward and backward the lower-jaw side attachment can be changed by fixing the bolt member retainer at the specified angle. Therefore, for example, the lower-jaw side attachment and the lower jaw can be drawn obliquely upwardly, whereby an airway is maintained widely for the drawing extent.

CAPTIONS FOR THE SYMBOLS

K1, K2: Airway maintenance apparatus
1: Upper-jaw side attachment
2: Lower-jaw side attachment
3: Stepless adjusting device
30: Bolt member retainer
300: Fitting member
301: Insertion member
302: Bent portion
303: Axial bolt for fixation
304: Nut
305: Connection portion
306: Bearing portion
31: Nut member
310: Fixing portion
311: Nut
32: Bolt member
320: Screw portion
321: Bolt head
322: Turn operation portion
4: Blocker

BEST MODE FOR EMBODYING THE INVENTION

Modes of embodiment of the present invention are hereinafter described in more detail with reference to the drawings.

Figure 1:
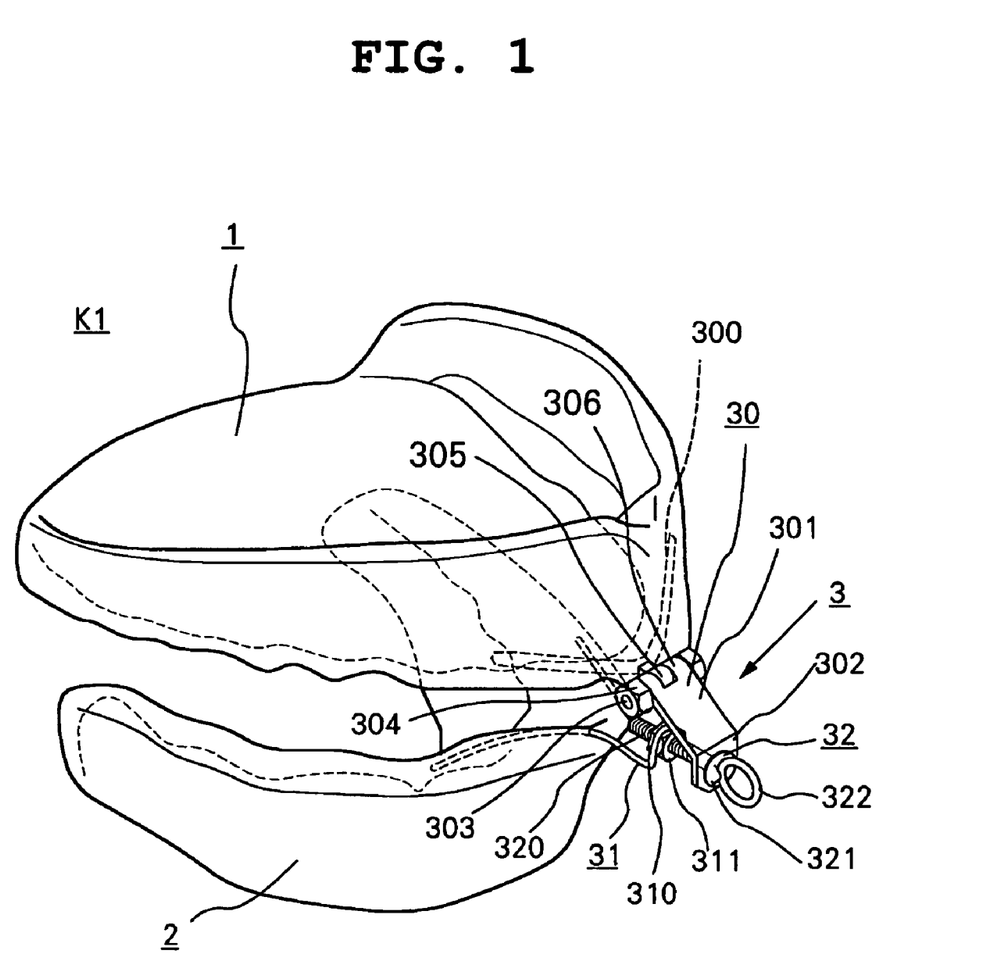
FIG. 1 is an exemplary perspective view showing the first mode of embodiment of the airway maintenance apparatus according to the present invention.

FIG. 1 is an exemplary perspective view showing the first mode of embodiment of the airway maintenance apparatus according to the present invention.

Figure 2:
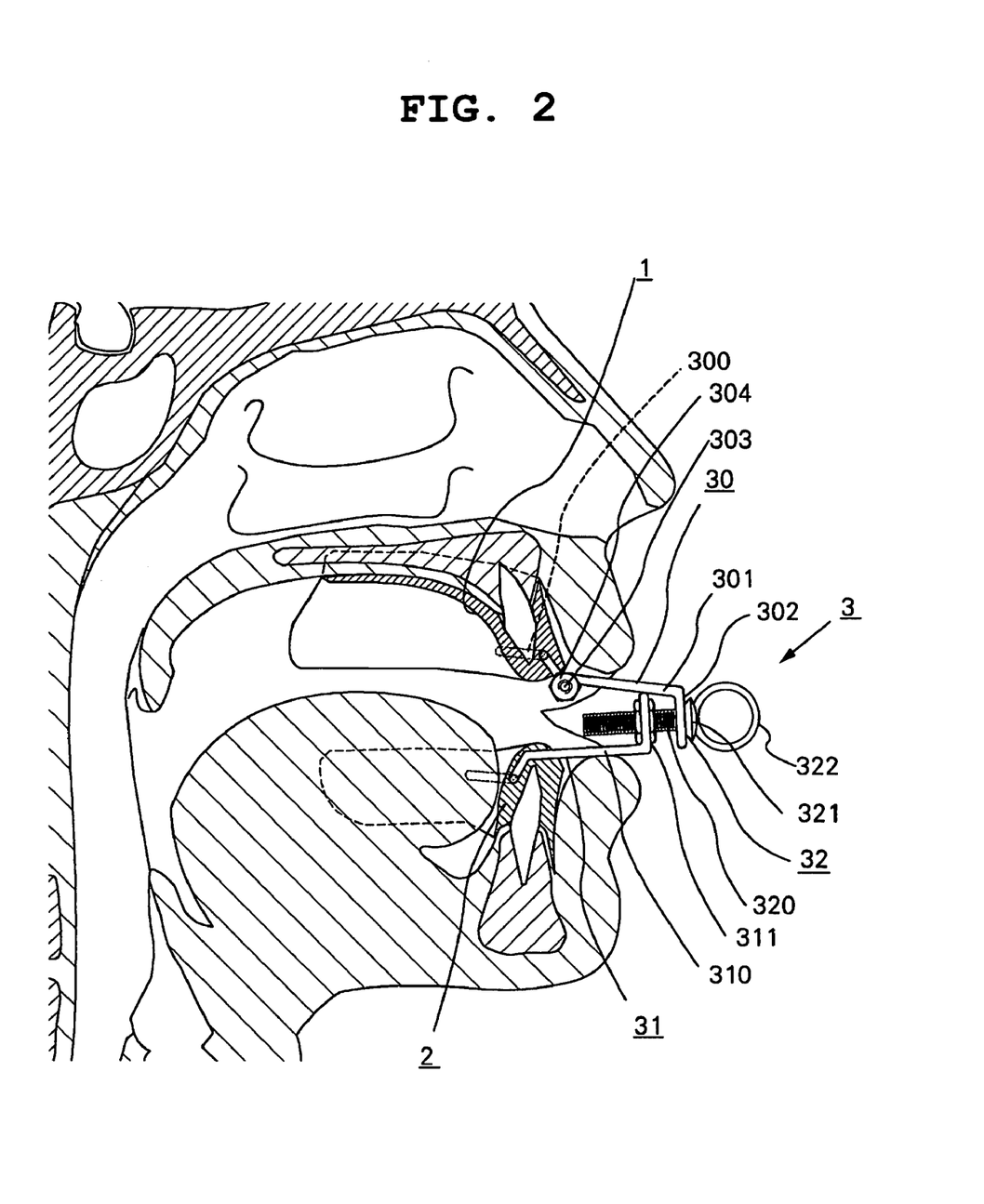
FIG. 2 is an exemplary enlarged cross-sectional view showing a state wherein the airway maintenance apparatus illustrated in FIG. 1 is attached to the oral cavity.

FIG. 2 is an exemplary enlarged cross-sectional view showing a state wherein the airway maintenance apparatus illustrated in FIG. 1 is attached to the oral cavity.

The airway maintenance apparatus K1 comprises an upper-jaw side attachment 1 and a lower-jaw side attachment 2. The upper-jaw side attachment 1 is attached to the upper jaw side in the oral cavity, whereas the lower-jaw side attachment 2 is attached to the lower jaw side in the oral cavity. The upper-jaw side attachment 1 and the lower-jaw side attachment 2 are formed separately, and formed so that they can be attached as engaged in and fixed to the upper jaw side and the lower jaw side, respectively, with substantially no gap formed between the attachments and teeth and gum. The upper-jaw side attachment 1 and the lower-jaw side attachment 2 are usually prepared by casting a synthetic resin into a mold made for each patient.

The upper-jaw side attachment 1 and the lower-jaw side attachment 2 are connected via a stepless adjusting device 3 provided on the front side. The stepless adjusting device 3 is configured with a bolt member retainer 30 to be mounted on the upper-jaw side attachment 1, a nut member 31 to be mounted on the lower-jaw side attachment 2, and a bolt member 32 that links the bolt member retainer 30 and the nut member 31.

The stepless adjusting device 3 is described in detail below.

The bolt member retainer 30 comprises a fitting member 300 to be fixed to the upper-jaw side attachment 1 and a insertion member 301 to be provided in connection with the fitting member 300. The fitting member 300 is embedded in the upper-jaw side attachment 1 so that a connection portion 305 having an annular shape is protruded.

The insertion member 301 is formed with a rigid or semi-rigid thin plate of metal, having a bearing portion 306 formed with a roll-like curvature on the base side. The bearing portion 306 is notched at almost the center thereof to allow the connection portion 305 of the fitting member 300 to be engaged therein with roughly no gap.

The insertion member 301 is connected to the fitting member 300 in a pivotable manner in an up and down direction by inserting an axial bolt 303 for fixation to the bearing portion 306 and the connection portion 305 from one side thereof, and providing a nut 304 for fixation at the other side, and can be fixed at a specified angle by screwing in the nut 304.

Provided on the tip side of the insertion member 301 is a bent portion 302, which is bent downward. Formed in the bent portion 302 is a through hole (invisible in the illustration) that can be penetrated by the screw portion 320 of the bolt member 32.

The nut member 31 comprises a fixing portion 310 to be embedded in the lower-jaw side attachment 2 on the base side thereof so that the tip side thereof is protruded, and a nut 311 secured at the tip portion of the fixing portion 310.

The bolt member 32 comprises a screw portion 320 that can be screwed in the nut 311 through the through hole of the bent portion 302, a bolt head 321 that stops upon contact with the surface of the bent portion 302, and a turn operation portion 322 provided in the bolt head 321. The turn operation portion 322 has a ring shape permitting easy pinching from outside, and is secured upright to the surface of the bolt head 321.

The bolt member 32 is set as screwed in the nut 311 by penetrating the screw portion 320 through the through hole of the bent portion 302 from outside. The upper-jaw side attachment 1 and the lower-jaw side attachment 2 are connected in a state wherein a small gap is formed therebetween by the stepless adjusting device 3 (see FIG. 1).

The insertion member 301 shown in this mode of embodiment is formed with metal, but this is not to be construed as limiting, as long as the material is rigid or semi-rigid; for example, a synthetic resin and the like can also be used.

(Effect)

Figure 3:
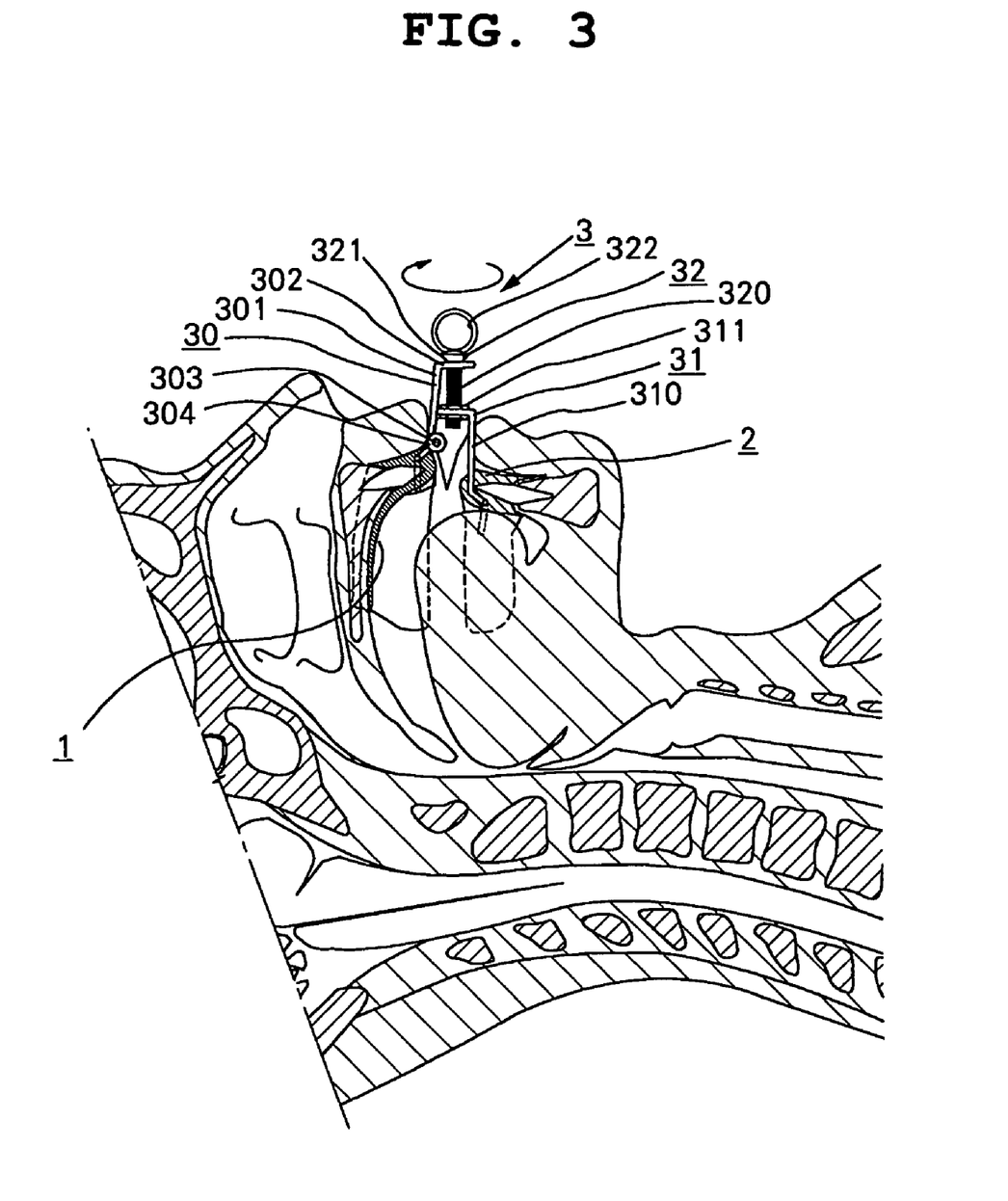
FIG. 3 is an exemplary cross-sectional view showing a state prior to drawing forward the lower-jaw side attachment.

FIG. 3 is an exemplary cross-sectional view showing a state prior to drawing the lower-jaw side attachment.

Figure 4:
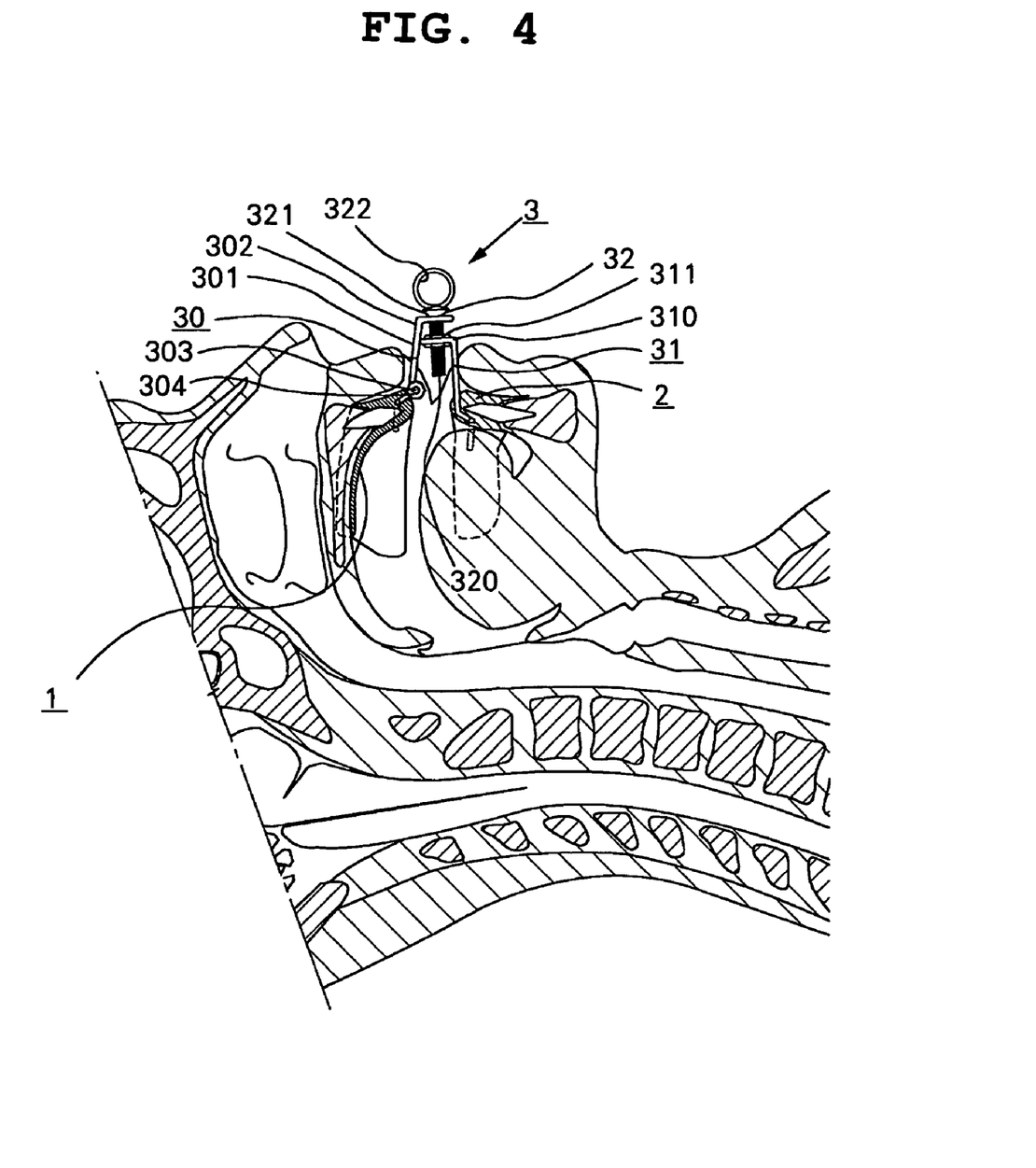
FIG. 4 is an exemplary cross-sectional view showing a state wherein the lower-jaw side attachment is drawn forward from the state illustrated in FIG. 3.

FIG. 4 is an exemplary cross-sectional view showing a state wherein the lower-jaw side attachment is drawn from the state illustrated in FIG. 3.

FIG. 3 and FIG. 4 show states wherein the patient is in decubitus. Referring to FIG. 1 to FIG. 4, the usage and effect of the airway maintenance apparatus K1 shown in this mode of embodiment are described.

The airway maintenance apparatus K1 is intended to slightly draw the lower jaw forward from the normal occlusal position to forcibly maintain an airway, so as to prevent apnea from occurring during sleep.

First, prior to attaching the airway maintenance apparatus K1, the upper-jaw side attachment 1 and the lower-jaw side attachment 2 are connected with the bolt member 32. At the same time, the nut 311 is fitted to the tip side of the screw portion 320 so that the upper-jaw side attachment 2 is arranged slightly backward (inside) from the upper-jaw side attachment 1 before attaching the apparatus.

The upper-jaw side attachment 1 and the lower-jaw side attachment 2 are attached to the upper jaw side and the lower jaw side in the patient's oral cavity, and fixed (see FIG. 3). Formed between the upper-jaw side attachment 1 and the lower-jaw side attachment 2 is a slight gap by the stepless adjusting device 3. On the back tooth side, the upper-jaw side attachment 1 and the lower-jaw side attachment 2 may come in contact with each other.

After attaching the upper-jaw side attachment 1 and the lower-jaw side attachment 2, the insertion member 301 is pivoted to have a specified angle relative to the fitting member 300, and the nut 304 is fastened to fix the apparatus at the angle. Specifically, the apparatus is fixed by slightly pivoting the insertion member toward the nose side to lift the lower-jaw side attachment 2 obliquely upwardly (toward the nose side).

Then, the bolt member 32 is turned clockwise (right direction) by a third person (for example, physician, nurse). The bolt member 32 is operated by pinching and turning the turn operation portion 322. Thus, the nut 311 fitted to the tip side of the screw portion 320 is moved for a specified distance toward the bent portion 302 side along with the screw portion 320 (see FIG. 4).

As the nut 311 moves toward the bent portion 302 side, the lower-jaw side attachment 2 and the lower jaw wearing the same are drawn forward for the same distance as the movement of the nut 311 relative to the upper-jaw side attachment 1. At this time, the lower-jaw side attachment 2 and the lower jaw are drawn obliquely upwardly (toward the nose side) because the insertion member 301 is fixed with a slight rotation toward the nose side. The lower-jaw side attachment 2 is drawn forward while in a state attached with a slight gap formed between the same and the upper-jaw side attachment 1.

Since the bolt member 32 is provided so that it will penetrate the penetration portion of the bent portion 302 and stop with the bolt head 321 in contact with the surface of the bent portion 302, the bolt member can move around the penetration portion as the fulcrum. Hence, even while wearing the lower-jaw side attachment 2, the lower jaw can be moved slightly but effectively to lessen the sensation of restraint.

Note that there are no well-established standards and the like for the drawing extents for the nut 311 and the lower-jaw side attachment 2; the widths are set on the basis of a third party's experience, intuition and the like, as long as no significant burden is exerted on the patient. Therefore, in this state, it remains unknown whether or not an airway is maintained. In this case, usually, the drawing extent is set at a position that seems to maintain an airway. Then, the patient is asked to sleep.

In the patient falling asleep while wearing the airway maintenance apparatus K1, apnea occurs if an airway is not maintained in an appropriate state. In the event of apnea, a third party operates the bolt member 32 to draw forward or push in the lower-jaw side attachment 2. The drawing extent for the lower-jaw side attachment 2 can be adjusted in a stepless manner by moving the nut 311 along with the screw portion 320. Additionally, because the drawing extent can be adjusted in a stepless manner, the lower-jaw side attachment 2 and the lower jaw are moved smoothly. Thus, an appropriate position of the lower-jaw side attachment 2 to maintain an airway can be found, and the occurrence of apnea can be prevented.

Hence, according to the airway maintenance apparatus K1, because the lower-jaw side attachment 2 can be drawn forward and pushed in relative to the upper-jaw side attachment 1 by operating the bolt member 32 from outside, a drawing extent for the lower-jaw side attachment 2 suitable for each patient can be quickly and easily set.

Since the airway maintenance apparatus K1 allows stepless adjustment of the drawing extent for the lower-jaw side attachment 2, the drawing extent relative to the upper-jaw side attachment can be easily changed little by little, and hence, the apparatus accommodates many patients.

The airway maintenance apparatus K1 can be drawn forward while wearing the upper-jaw side attachment 1 and the lower-jaw side attachment 2 because the lower-jaw side attachment 2 is attached with a slight gap formed between the same and the upper-jaw side attachment 1. Hence, the drawing extent can be adjusted without waking up the patient in sleep because the airway maintenance apparatus K1 is not taken out from the oral cavity at the time the drawing extent is adjusted.

Additionally, because a slight gap is formed between the upper-jaw side attachment 1 and the lower-jaw side attachment 2 as described above, the oral cavity is already enlarged at the time the attachments are attached, and hence the airway maintenance apparatus K1 is not easily disengaged.

Meanwhile, the present inventor investigated and found that the amount of change in airway patency for the same drawing extent differs depending on the direction of drawing the lower jaw. Although individual differences may exist, a specific example is given. For example, relative to a 100% patency obtained when the lower jaw was drawn obliquely upwardly, the airway could be opened by 93.89% when the lower jaw was drawn laterally (roughly horizontally), and only by 85.21% when the lower jaw was drawn obliquely downwardly.

Since the airway maintenance apparatus K1 is configured so that the insertion member 301 can pivot and be fixed at a specified angle, the lower-jaw side attachment 2 and the lower jaw can be drawn obliquely upwardly by fixing the insertion member with a slight rotation toward the nose side. Hence, the burden on the patient can be lessened because the airway maintenance apparatus K1 is capable of maintaining a wide airway for the drawing extent by drawing the lower jaw obliquely upwardly.

In this mode of embodiment, the upper-jaw side attachment 1 and the lower-jaw side attachment 2 are attached to the oral cavity while connected in advance, but this is not to be construed as limiting; for example, the upper-jaw side attachment 1 and the lower-jaw side attachment 2 may be separately attached to the oral cavity and then connected by screwing the bolt member 32 in the nut 311.

In this mode of embodiment, the patient sleeps with the lower-jaw side attachment 2 drawn forward to some extent, but this is not to be construed as limiting; for example, the patient may fall asleep without drawing forward the lower-jaw side attachment 2, which is drawn forward upon onset of apnea.

In this mode of embodiment, the bolt member retainer 30 is mounted on the upper-jaw side attachment 1, and the nut member 31 is fitted to the lower-jaw side attachment 2, but this is not to be construed as limiting; provided that the bolt member 32 is provided so that it does not move axially relative to the bolt member retainer 30, the nut member 31 may be fitted to the upper-jaw side attachment 1, and the bolt member retainer 30 may be mounted on the lower-jaw side attachment 2.

Figure 5:
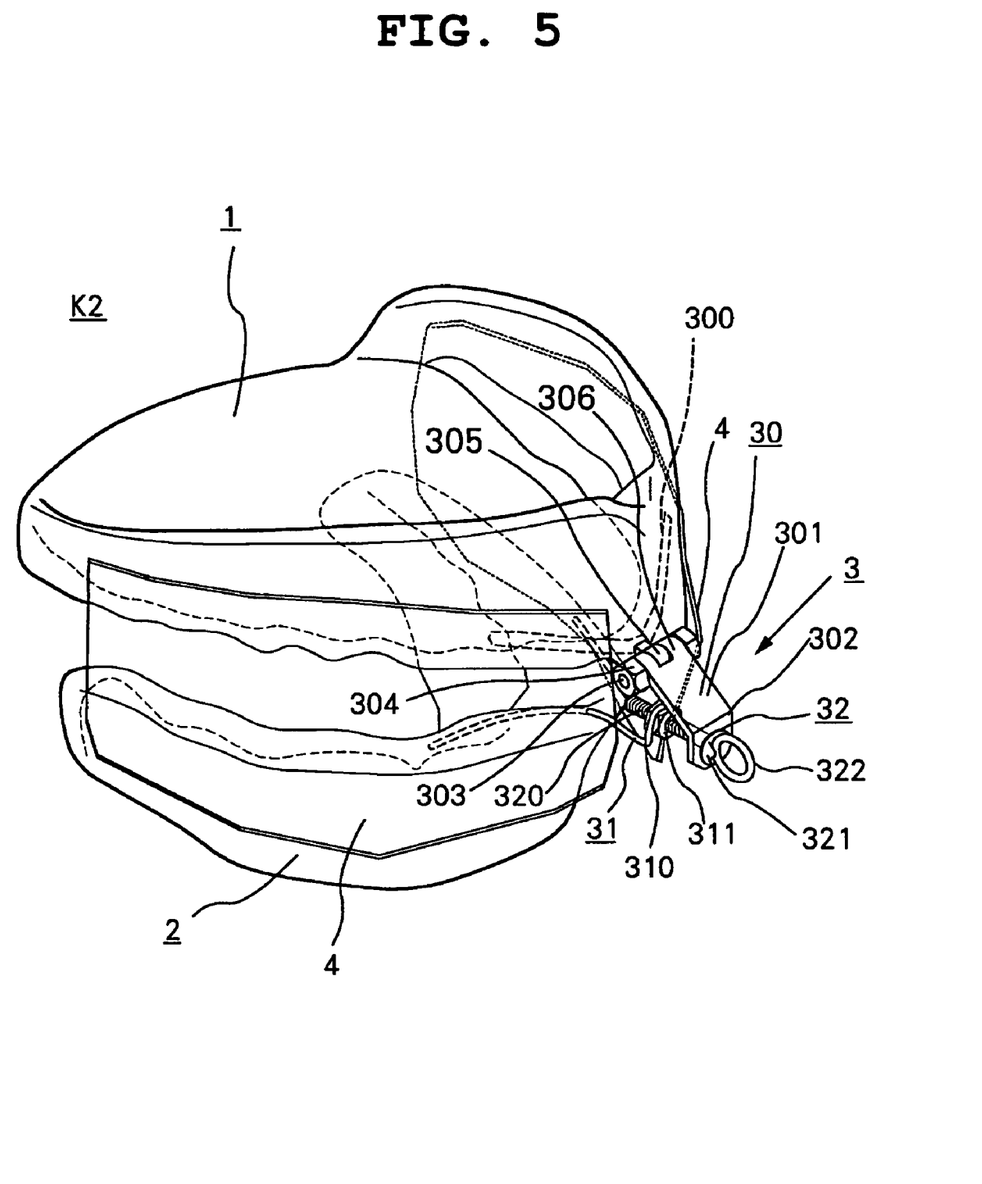
FIG. 5 is an exemplary perspective view showing the second mode of embodiment of the airway maintenance apparatus according to the present invention.

FIG. 5 is an exemplary perspective view showing the second mode of embodiment of the airway maintenance apparatus according to the present invention.

In FIG. 5, the same symbols are given to the same or equivalent portions as those shown in FIG. 1 to FIG. 4 above. Additionally, in the description below, explanations on structure that duplicate those for the portions shown above are omitted except for essential matters.

Fitted to the upper-jaw side attachment 1 as a component of the airway maintenance apparatus K2 is a blocker 4 as a blocker that substantially blocks the gap between the upper-jaw side attachment 1 and the lower-jaw side attachment 2 formed at the time the apparatus is attached. The blocker 4 is provided in an outer face of the upper-jaw side attachment 1 other than the front fact, to which the bolt member retainer 30 is fitted, so that it is suspended over the outside of the lower-jaw side attachment 2 during use.

(Effect)

Referring to FIG. 5, the effect of the airway maintenance apparatus K2 in the second mode of embodiment is described.

Regarding similar effects and actions resulting from configurations common to the above-described airway maintenance apparatus K1, explanations are omitted, with only different features described here.

According to the airway maintenance apparatus K2, because the blocker 4 can substantially block the gap between the upper-jaw side attachment 1 and the lower-jaw side attachment 2 formed at the time the apparatus is attached, it is possible to prevent dryness in the oral cavity during sleep, and to prevent entry of foreign matter in the oral cavity.

In this mode of embodiment, the blocker 4 is formed with the same material (synthetic resin) as the material that constitutes the upper-jaw side attachment 1, but this is not to be construed as limiting; for example, metal can be used. The blocker 4 can also be designed to, for example, have a small through hole to allow some extent of the passage of air.

The upper-jaw side attachment 1 and the lower-jaw side attachment 2 shown in the above-described airway maintenance apparatuses K1 and K2 are prepared by casting a synthetic resin into a mold made for each patient, but this is not to be construed as limiting; for example, the portion coming in contact with the upper jaw or the lower jaw may be formed with a thermoplastic synthetic resin. In this case, an upper-jaw side attachment 1 and a lower-jaw side attachment 2 fitting each patient can be formed by fitting the resin in a thermally softened state to the upper jaw and the lower jaw, and then cooling the resin to solidify. Hence, the airway maintenance apparatus can be mass-produced.

The terms and phrases used herein are for illustrative purposes, are not to be construed as limiting, and are not intended to exclude terms and phrases equivalent to the features described herein and part thereof. Additionally, various modified modes are of course possible within the scope of the technical idea of the present invention.

The invention claimed is:

1. An airway maintenance apparatus for drawing a lower jaw forward to forcibly maintain an airway, the airway maintenance apparatus comprising:

an upper-jaw side attachment to be attached to the upper jaw side in the oral cavity, and a lower-jaw side attachment to be attached to the lower jaw side in the oral cavity, provided separately from the upper jaw side attachment, wherein the lower-jaw side attachment is connected to the upper-jaw side attachment via a stepless adjusting device capable of moving in a stepless manner in the direction of drawing the lower jaw forward relative to the upper-jaw side attachment, the stepless adjusting device comprising:

a bolt member provided with a turn operating portion at one end of a screw portion thereof, a bolt member retainer mounted on the upper-jaw side attachment in a vertically rotatable manner, and formed to allow the penetration of the screw portion of the bolt member, and not to allow the penetration of the turn operation portion, a nut member mounted on the lower-jaw side attachment, in which the screw portion of the bolt member penetrating the bolt member retainer can be screwed, and a fixing device, having an axial bolt and a nut, for fixing the bolt member retainer to the upper jaw side attachment at a specified angle, wherein the bolt member is formed not to allow axial movement thereof, relative to the bolt member retainer, and so that the lower-jaw side attachment can be moved forward and backward relative to the upper jaw side attachment by turning the bolt member, in a state where the bolt member is screwed into the nut member, the vertically rotatable manner of the bolt member retainer and the fixing device enables the bolt member retainer to be fixed at an angle, thereby permitting drawing of the lower jaw obliquely upward.

2. The airway maintenance apparatus of claim 1, which is provided with a blocker that blocks or substantially blocks the gap between the upper jaw side attachment and the lower jaw side attachment formed at the time they are attached.

3. A stepless adjusting device to be mounted on an airway maintenance apparatus comprising an upper-jaw side attachment to be attached to the upper jaw side in the oral cavity, and a lower-jaw side attachment to be attached to the lower jaw side in the oral cavity, provided separately from the upper-jaw side attachment, wherein the lower-jaw side attachment is connected to the upper-jaw side attachment via the stepless adjusting device capable of moving in a stepless manner in the direction of drawing the lower jaw forward relative to the upper-jaw side attachment, the stepless adjusting device comprising:

a bolt member provided with a turn operation portion at one end of a screw portion thereof, a bolt member retainer mounted on the upper jaw side attachment in a vertically rotatable manner, and formed to allow the penetration of the screw portion of the bolt member, and not to allow the penetration of the turn operation portion, a nut member mounted on the lower-jaw side attachment, in which the screw portion of the bolt member penetrating the bolt member retainer can be screwed, and a fixing device, having an axial bolt and a nut, for fixing the bolt member retainer to the upper jaw side attachment at a specified angle, wherein the bolt member is formed not to allow axial movement thereof, relative to the bolt member retainer, and so that the lower-jaw side attachment can be moved forward and backward relative to the upper jaw side attachment by turning the bolt member, in a state where the bolt member is screwed into the nut member, the vertically rotatable manner of the bolt member retainer and said fixing means enables the bolt member retainer to be fixed at an angle, thereby permitting drawing of the lower jaw obliquely upward.

4. A stepless adjusting device to be mounted on an airway maintenance apparatus comprising an upper-jaw side attachment to be attached to the upper jaw side in the oral cavity, a lower-jaw side attachment to be attached to the lower jaw side in the oral cavity, provided separately from the upper-jaw side attachment, and a blocker that blocks or substantially blocks the gap between the upper jaw side attachment and the lower-jaw side attachment formed at the time they are attached, wherein the lower-jaw side attachment is connected to the upper-jaw side attachment via the stepless adjusting device capable of moving in a stepless manner in the direction of drawing the lower jaw forward relative to the upper-jaw side attachment, the stepless adjusting device comprising:

a bolt member provided with a turn operation portion at one end of a screw portion thereof, a bolt member retainer mounted on the upper jaw side attachment in a vertically rotatable manner, and formed to allow the penetration of the screw portion of the bolt member, and not to allow the penetration of the turn operation portion, a nut member mounted on the lower-jaw side attachment, in which the screw portion of the bolt member penetrating the bolt member retainer can be screwed, and a fixing device, having an axial bolt and a nut for fixing the bolt member retainer to the upper-jaw side attachment at a specified angle, wherein the bolt member is formed not to allow axial movement thereof relative to the bolt member retainer, and so that the lower-jaw side attachment can be moved forward and backward relative to the upper jaw side attachment by turning the bolt member in a state where the bolt member is screwed into the nut member, the vertically rotatable manner of the bolt member retainer and the fixing device enables the bolt member retainer to be fixed at an angle, thereby permitting drawing of the lower jaw obliquely upward.

* * * * *